(12) United States Patent
Brown

(10) Patent No.: US 9,482,623 B2
(45) Date of Patent: Nov. 1, 2016

(54) TEST DEVICE AND METHOD

(75) Inventor: Robin Brown, Bedford (GB)

(73) Assignee: SPD SWISS PRECISION DIAGNOSTICS GMBH, Geneva (CH)

( * ) Notice: Subject to any disclaimer, the term of this patent is extended or adjusted under 35 U.S.C. 154(b) by 522 days.

(21) Appl. No.: 13/502,483

(22) PCT Filed: Oct. 21, 2010

(86) PCT No.: PCT/GB2010/001958
§ 371 (c)(1),
(2), (4) Date: Jun. 26, 2012

(87) PCT Pub. No.: WO2011/048381
PCT Pub. Date: Apr. 28, 2011

(65) Prior Publication Data
US 2012/0321519 A1      Dec. 20, 2012

(30) Foreign Application Priority Data

Oct. 21, 2009 (GB) .................. 0918462.3

(51) Int. Cl.
*B01L 3/00* (2006.01)
*G01N 21/84* (2006.01)
*G01N 33/53* (2006.01)

(52) U.S. Cl.
CPC ............ *G01N 21/8483* (2013.01); *B01L 3/50* (2013.01); *B01L 3/5029* (2013.01); *B01L 3/502715* (2013.01)

(58) Field of Classification Search
None
See application file for complete search history.

(56) References Cited

U.S. PATENT DOCUMENTS

| | | |
|---|---|---|
| 4,937,050 A | 6/1990 | Meinecke et al. |
| 5,091,154 A | 2/1992 | Pauli et al. |
| 6,043,880 A | 3/2000 | Andrews et al. |
| 2002/0009391 A1 | 1/2002 | Marquiss et al. |
| 2005/0142033 A1 | 6/2005 | Glezer et al. |
| 2008/0053201 A1 | 3/2008 | Roesicke et al. |
| 2011/0263006 A1* | 10/2011 | Chan et al. ............... 435/287.1 |

FOREIGN PATENT DOCUMENTS

| | | |
|---|---|---|
| DE | 3112029 A1 | 10/1982 |
| EP | 0833145 A1 | 4/1998 |
| EP | 1484601 A2 | 12/2004 |
| WO | WO-03042048 A2 | 5/2003 |
| WO | WO-2004077031 A1 | 9/2004 |
| WO | WO-2008134811 A1 | 11/2008 |

\* cited by examiner

*Primary Examiner* — Neil N Turk

(74) *Attorney, Agent, or Firm* — David Halstead; Erik Huestis; Foley Hoag LLP

(57) ABSTRACT

A connection assembly for a test device comprises a carriage for receiving at least a portion of a test device and a receptacle for co-operation with the carriage. The carriage is longitudinally movable with respect to the receptacle and is latchable to the receptacle at a predetermined position.

24 Claims, 12 Drawing Sheets

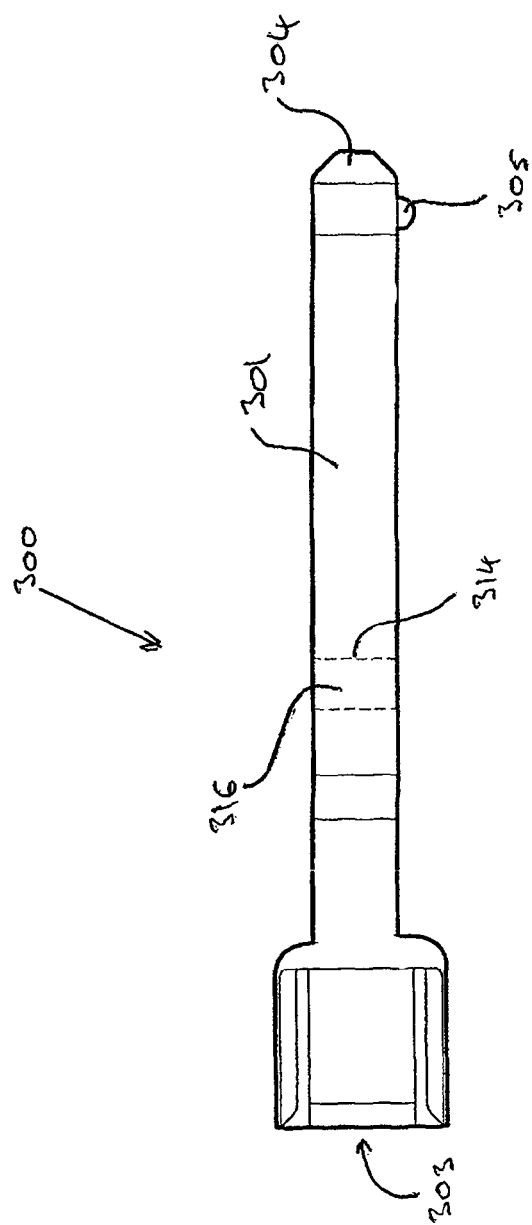

Figure 5A.
Figure 5B.
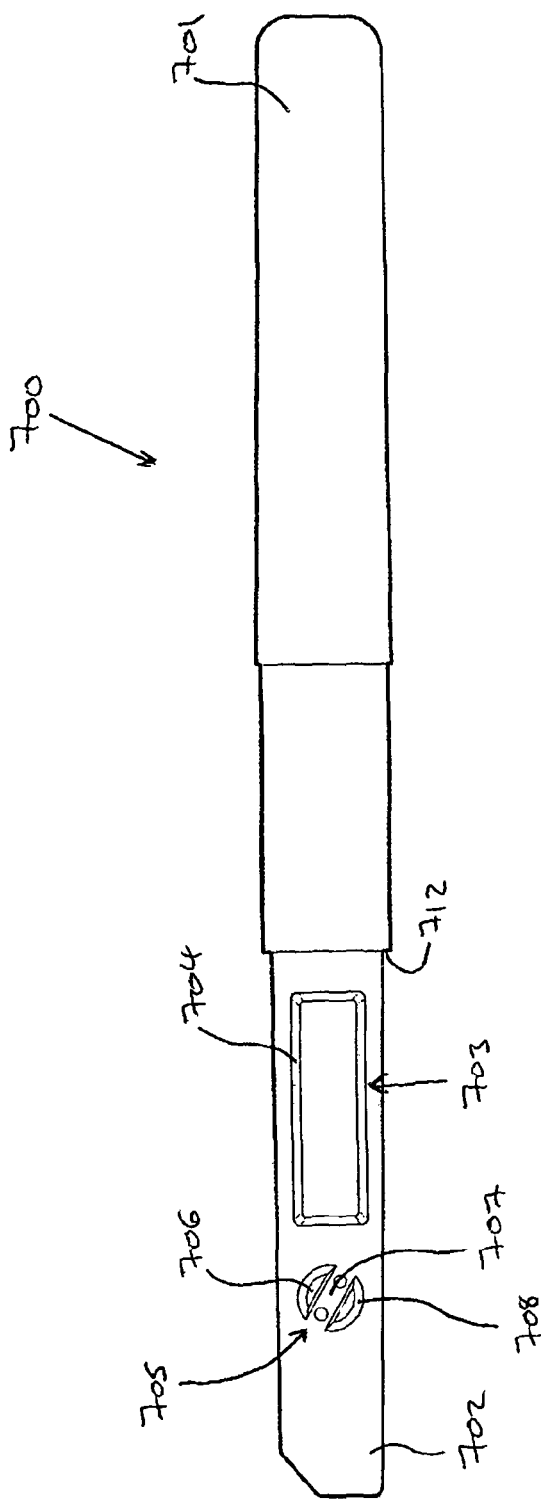
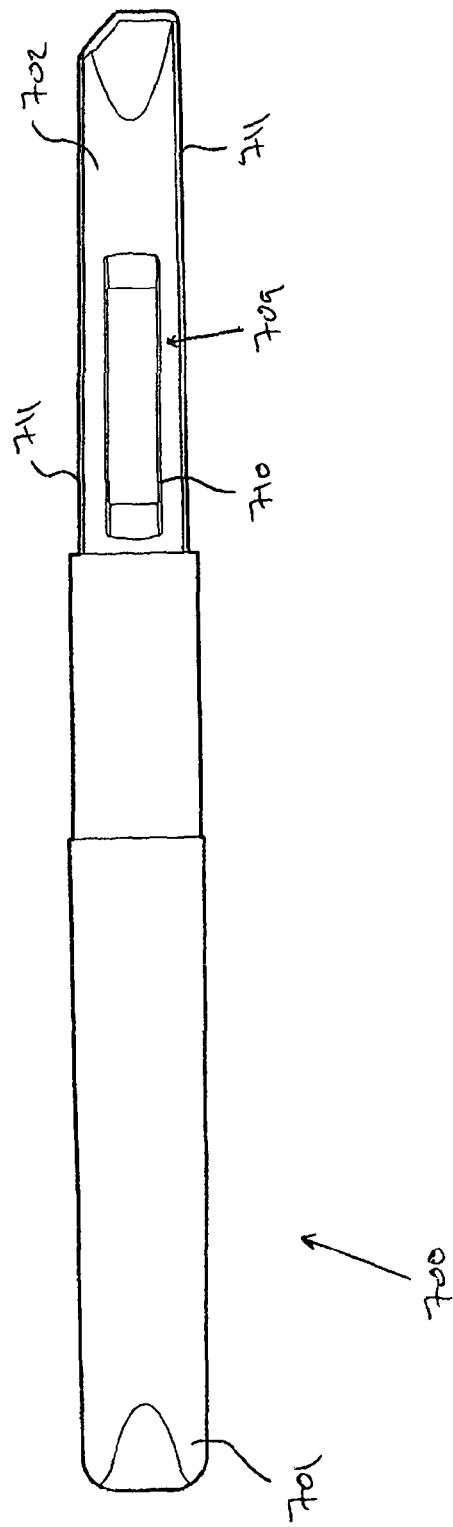

TEST DEVICE AND METHOD

CROSS-REFERENCE TO RELATED APPLICATIONS

This application is a national-stage filing under 35 U.S.C. §371 of International Application No. PCT/GB2010/001958, filed Oct. 21, 2010, which claims the benefit of Great Britain Application No. 0918462.3, filed Oct. 21, 2009. International Application No. PCT/GB2010/001958 was published under PCT Article 21(2) in English.

The present invention relates to the field of testing. An embodiment relates to a reader; another to a test kit; another to a connection assembly for test apparatus for testing sample material, and another to a method of testing.

Various medical diagnostic products are known which analyse a fluid sample, such as urine or blood, to determine the presence or amount of one or more analytes. These may be small, handheld devices, which are used by applying the sample to an absorbent component; the devices are configured to subsequently convey the fluid to an internal assay test zone, e.g. by capillary action. There is little risk of spillage of the sample out of the device during the assay. Examples include pregnancy tests, ovulation tests and fertility tests.

Many such products are one-piece, visually-read devices in which an elongate test strip incorporating assay reagents is provided in a housing, with a sample application region at one end of the device and a window in the housing towards the other end of the device through which the test zone and thereby the result of the assay can be seen. Recently, however, there has been a trend towards digitally-read devices, which remove any element of interpretation of the result needed by the user or medical professional. These may be two-piece kits, the test strip being incorporated in one type of assay device known as a test stick, which is inserted into a cavity ("test bay") of a separate reader to digitally read the assay result via optical or other reading elements. The test stick is generally a low cost, disposable element, whereas the reader is more sophisticated and may be reusable.

In such kits, it is generally important to ensure that the appropriate regions of the test strip are correctly aligned with the reading elements. An extremely high level of precision of positioning is desired to maximise accuracy, especially when the assay results in the appearance of, or change in, one or more thin lines on the test strip which must be detected by the reading elements. Desirably, therefore, the kit should include features which guarantee accurate positioning of the test strip each time, even when used by an unskilled user.

Products are available in which the reader is to be used many times over (e.g. for a woman to obtain information about her hormone levels for contraceptive purposes or for monitoring fertility over a longer period of time), and in these products it is desirable to be able to access the test bay area for cleaning.

EP-A-833145 describes one such product in which the test bay is formed by a recess in the surface of the reader to receive the test stick but not completely enclose it, so that the test bay is accessible for cleaning. A "lock and key" location feature and combined switch actuation mechanism is provided inside the test bay, which engages with a corresponding mating feature on the test stick.

In the invention of EP-A-833145, the insertion of the test stick in the reader is achieved in stages. Initially, the test stick is held inclined with respect to a flat floor of the test bay. The user then applies a linear movement whereby an end of the test stick is placed beneath a canopy of the test bay. Subsequently, the user applies a rotational movement whereby the test stick pivots about a fulcrum at a lip of the canopy and snaps past a pair of projecting spring-loaded buttons into a horizontal position. In this horizontal position, the test stick is parallel with the floor of the test bay.

Although these features designed to facilitate correct interaction between the test stick and the reader are effective to an extent, this device does not afford extreme accuracy of location because it is vulnerable to the effects of very slight manufacturing variations in the elements involved. Thus, the test stick may be fractionally out of place, even when used correctly by the user.

Furthermore, it suffers from additional problems. Firstly, it is possible to insert the test stick into the test bay in the wrong orientation, with a little force. Secondly, even when the test stick is inserted the right way around, the spring-loaded mechanism does not prevent it from sticking slightly out of its correct longitudinal alignment.

Thirdly, the pivoting movement of the test stick about the fulcrum at the lip of the canopy, in combination with the force of the spring-loaded buttons pressing the test stick hard against the sharp edges of the location feature, could result in wear of the location feature due to friction over the many times a test stick is inserted and removed during the lifetime of the kit. This wear may produce stray particles which are liable to contaminate the kit, potentially having a detrimental affect on the test results, as well as causing reliability issues by clogging the switch actuation mechanism which is incorporated into the location feature. It also adds to the existing problems in achieving the required repeatable accuracy of positioning of the test stick relative to the reader.

Products are available in which the reader is an elongate device having a test bay into which the appropriate end of the test stick is inserted and completely enclosed, such as the device illustrated in EP-A-1484601. A "lock and key" location feature and combined switch actuation mechanism, of the same type described in EP-A-833145, is provided inside the test bay which engages with a corresponding mating feature on the test stick. The test bay is formed by two case halves, one half being slidable and acting as a carriage to guide the test stick gently into position with the assistance of runners and an elastic band, upon application of a linear insertion force by the user. The carriage releasably clicks into place on the other case half when the test stick has been inserted the correct distance and the location features are engaged.

This design is preferred for applications in which the reader is used only once or only a limited number of times, such as for pregnancy tests or ovulation tests. Wear of the device is not a major problem, but there is room for improvement in terms of the precision positioning desired, because it is still subject to the same problems caused by slight manufacturing variations described above.

It will be recognised that such problems could be experienced by other similar test kits in which the assay device is not in a "stick" format.

There is therefore a need in the art for a test kit comprising an assay device and a reader that affords extreme accuracy of positioning of the assay device relative to the reader.

According to a first aspect, there is provided a reader for determining the presence and/or amount of one or more analytes in a sample carried by an assay device, said reader optionally comprising a carriage for at least a portion of the assay device; wherein the reader is adapted to receive at least a portion of the assay device into a cavity thereof; the reader comprising magnetic means for latching the assay device onto the reader within said cavity at a predetermined reading position, said latching either being direct latching or via latching of the carriage onto the reader.

According to a second aspect, there is provided a test kit for determining the presence and/or amount of one or more analytes in a sample, comprising an assay device and a reader, said reader optionally comprising a carriage for at least a portion of the assay device; wherein the reader is adapted to receive at least a portion of the assay device into a cavity thereof; and the kit comprises magnetic means for latching the assay device onto the reader within said cavity at a predetermined reading position, said latching either being direct latching or via latching of the carriage onto the reader.

Some embodiments include a carriage. In others there is no carriage. When the carriage is present, in an embodiment it is shaped and sized to carry the assay device such that latching of the carriage to the reader conveys the assay device to the reading position. In another embodiment, the carriage comprises means to latch the assay device onto itself, such as magnetic means co-operating with corresponding magnetic means of the assay device, or physical engagement of corresponding location features on the assay device and carriage.

In a test kit of the second aspect, performing an assay for the one or more analytes may cause a change to occur at a test zone of the assay device, said change only being detectable by the reader when the assay device is located at the predetermined reading position. In an embodiment, the change comprises the appearance, disappearance or change in intensity of a line in the test zone.

In an embodiment, the magnetic means is one or more permanent magnets. Advantageously, the magnets are small relative to the size of the test zone, to improve accuracy. When the change relates to a line at the test zone, the magnets are preferably no more than 5 times the width of the line, preferably no more than 4 times this width, preferably no more than 3 times this width.

The reader may comprise optical reading means, which may comprise a light source system such as one or more LEDs and a sensor system such as one or more photodiodes. In an embodiment, the reader determines the presence and/or amount of one or more analytes in the sample using optical transmission through the test zone. In another embodiment, the reader utilises optical reflection from the test zone.

The assay device may comprise a porous carrier and/or microfluidic flow path.

In different embodiments one or more magnetic means are provided in or adjacent the cavity, which co-operate with one or more magnetic means on the assay device itself and/or on the carriage for the assay device.

The reader may comprise a carriage for receiving at least a portion of the assay device in its interior, and the carriage is adapted to be received in the cavity of the reader. The carriage may be detachable from the reader or it may be secured in the cavity in a non detachable fashion, whilst still being able to move within the cavity.

The reader may comprise a carriage for at least a portion of the assay device, and the carriage forms at least one wall of the cavity.

In an embodiment, the reader is adapted to allow movement of the assay device in two dimensions within the cavity. Preferably, movement of the assay device in one dimension is effected by a force applied by the user. In addition, the attractive force between the magnetic means on the reader and the magnetic means on the assay device (and/or between the magnetic means on the reader and the magnetic means on the carriage) contributes to effecting movement of the assay device in another dimension. Other features may be present to assist movement in the second dimension, such as a narrowing of one side of the cavity in the direction of insertion of the assay device, which can help to guide the assay device into the reading position.

In some embodiments, application of a linear force by the user causes the assay device to move inwardly of the reader, and the assay device also moves orthogonally to the force direction.

The reader may contain a protrusion in the cavity, which mates with a recess in the assay device and/or carriage, if present, when the assay device is located at the predetermined reading position. In an embodiment, it mates with a recess in the assay device.

The reader may comprise means for latching the assay device and/or carriage onto the reader within said cavity at a predetermined pre-reading and/or post-reading position that is spaced apart from the reading position, and preferably also spaced apart from the protrusion, if present. This is particularly useful when the carriage is present but detachable from the reader. It can also be used to advantage to control the way in which the assay device and/or carriage is presented to the protrusion, if present.

Where a carriage is present the pre-/post-reading position and the reading position may be arranged such that the assay device and the carriage are conveyed in two dimensions between the pre-/post-reading position and the reading position, preferably upon application of a linear force.

In embodiments where no carriage is present, the pre-/post-reading position and the reading position may be arranged such that the assay device is conveyed in two dimensions between the pre-/post-reading position and the reading position, preferably upon application of a linear force.

In some embodiments there is a plurality of reading positions, for instance for determining the presence and/or amount of a plurality of analytes, and there may be a like number of magnetic means.

The walls of the reader may define the cavity.

In an embodiment there is provided a first magnet associated with the assay device; and a second magnet associated with the cavity, the first magnet being co-operable with the second magnet to latch the assay device at the predetermined position.

According to a third aspect there is provided a connection assembly comprising: a carriage for receiving at least a portion of an assay device; and a receptacle for co-operation with the carriage, wherein the carriage is movable with respect to the receptacle, the connection assembly further comprising magnetic means for latching the carriage to the receptacle at a predetermined position.

In an embodiment the carriage has a first magnetic means; and the receptacle has: a second magnetic means; and the receptacle has walls defining a cavity for receiving at least a portion of the carriage, and the first magnetic means is co-operable with the second magnetic means to latch the carriage to the receptacle at the predetermined position.

In an embodiment the connection assembly includes a plurality of predetermined positions.

In an embodiment the receptacle further comprises a third magnetic means longitudinally spaced from the second magnetic means, and the first magnetic means is co-operable with the third magnetic means to define a second position of the carriage relative to the receptacle.

In an embodiment the walls include opposing first and second walls and the carriage is laterally movable between the second position at the first wall and the predetermined position at the second wall.

In an embodiment the receptacle further comprises a formation for releasable engagement with an assay device in the predetermined position of the carriage, the formation being configured such that upon releasing the engagement the carriage is urged away from the second wall.

In an embodiment the receptacle is of unitary construction.

In an embodiment there is included a reading system for reading an assay device, the reading system defining a reading position corresponding to the predetermined position of the carriage relative to the receptacle.

In an embodiment there is included a coincident pre-reading/post-reading position corresponding to the second position.

Suitable sample materials for analysis by the reader include, but are not limited to, bodily fluids, e.g. urine, blood, oral fluid, saliva, sputum, breast milk, or vaginal fluids.

In a fourth aspect there is provided a connection assembly for test apparatus, the connection assembly comprising: a carriage and a receptacle, the carriage being configured to receive at least a portion of a test device, the carriage supporting carriage magnetic means; and the receptacle having a longitudinal axis and formed by opposing first and second walls defining therebetween a cavity; first magnetic means supported by the first wall and second magnetic means supported by the second wall, the third magnetic means being longitudinally spaced from the second magnetic means; the receptacle cavity being configured to receive at least a portion of the carriage, wherein: the carriage magnetic means and the first magnetic means are configured to latch the carriage to the receptacle at a first position where the carriage abuts the first wall; the carriage magnetic means and the second magnetic means are configured to define a second position of the carriage wherein the carriage abuts the second wall; and the carriage being longitudinally movable inside the cavity between the first and second positions.

According to a fifth aspect there is provided a method for using a connection assembly, the method comprising: introducing a test device to a carriage moveable with respect to a receptacle; and moving the carriage relative to the receptacle from a latched pre-reading/post-reading position to a latched reading position.

According to a sixth aspect there is provided a reader for reading a test stick, the reader having a housing, reading means arranged in the housing for co-operating with a said test stick and electronics responsive to an output of the reading means for giving an indication of information derived from the test stick, wherein the housing defines a receptacle and the reader has a carriage for receiving at least a portion of the test stick, and for carrying the test stick to a position where a reading zone of the test stick is adjacent the reading means for reading thereof, wherein the carriage is longitudinally movable within the receptacle, and the reader further comprises magnetic means for latching the carriage to the receptacle at said position.

According to a seventh aspect there is provided a reader for reading a test stick, the reader having a housing, optical detecting means arranged in the housing for co-operating with a said test stick and electronics responsive to an output of the optical detecting means for giving an indication of information derived from the test stick, wherein the housing defines a receptacle and the reader has a carriage for receiving at least a portion of the test stick, and carrying the test stick to a position where a reading zone of the test stick is adjacent the optical detecting means for reading thereof, wherein the carriage is longitudinally movable within the receptacle, and the reader further comprises magnetic means for latching the carriage to the receptacle at said position.

Embodiments will now be described, by way of example, with reference to the accompanying drawings in which:

FIG. 3 shows a plan view of the carriage of FIGS. 2A and 2B;

FIGS. 5A and 5B show side elevations of the assay device of FIGS. 2A and 2B;

Figure 1:
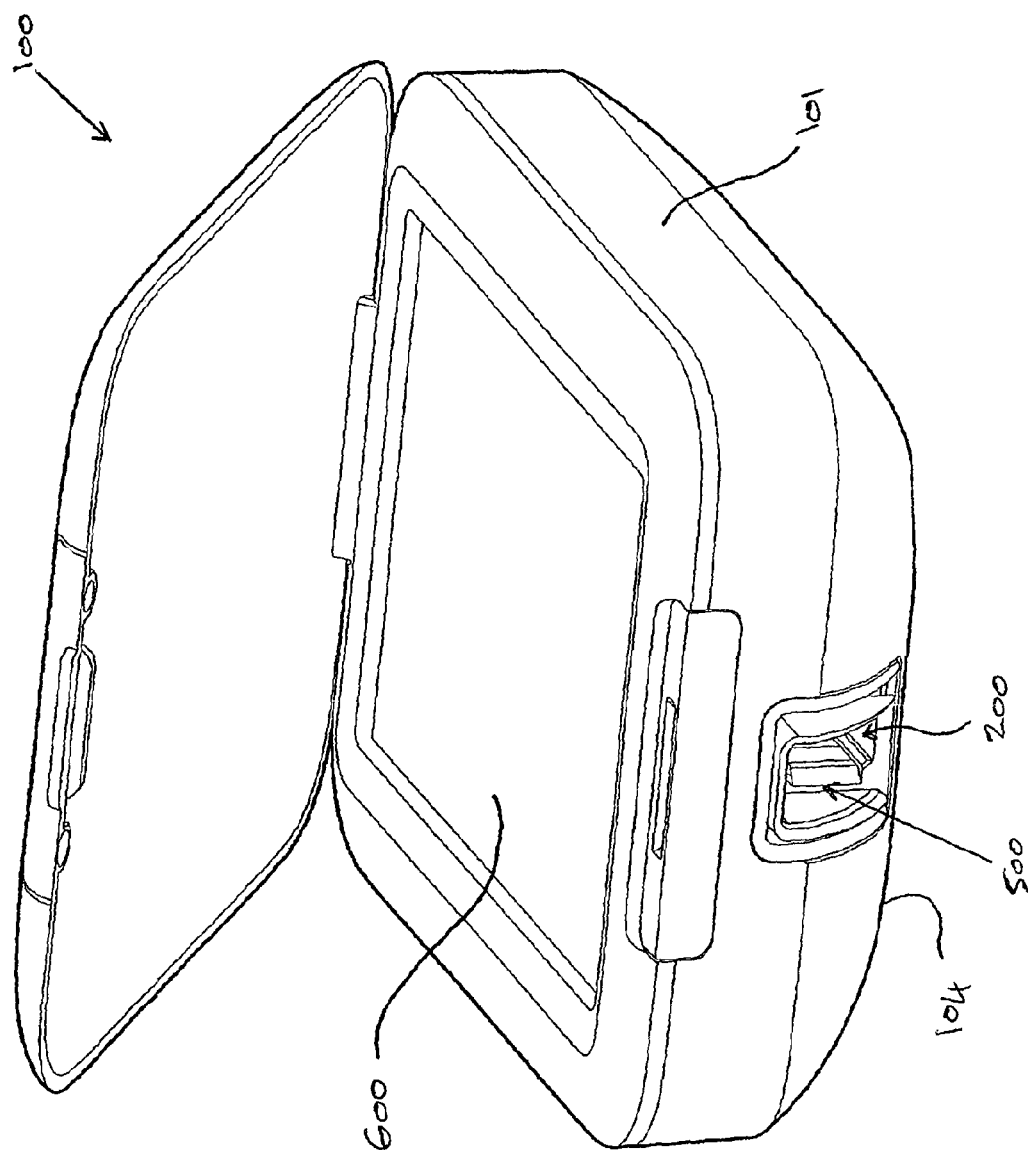
FIG. 1 shows a perspective view of test apparatus having a housing containing a connection assembly, a reading system and a display system.

The use of magnets or other magnetic means to control location of the assay device relative to the reading elements presents an advantage because such magnetic means can self-align in a precise fashion which compensates for any slight manufacturing variations in the various pieces of the kit.

In addition to controlling relative alignment of the assay device and the reading elements, it is also desirable to control the available optical paths and/or minimise the distance between those regions of the assay device and the reading elements, to provide an accurate test result. In many cases, therefore, the cavity of the reader into which the assay device is inserted bears a projection housing the reading elements, which at least partially fits into a window in the housing of the assay device. This projection achieves the latter aim and can also act as a "location feature" to an extent, but alone it generally does not afford sufficiently accurate positioning of the test stick.

When the projection into the test bay is along an axis different from the overall direction of insertion of the assay device (as is generally the case), the reader cannot be designed such that the inserted portion of the assay device forms a tight fit into the test bay (assuming that the projection is not made from a compressible material); extra room is required for the assay device to be able to move around and locate onto the projection. This causes additional challenges for the design of the mechanism of insertion (movement of the assay device in two dimensions is required) and for accurate positioning of the assay device (which has more room to move around inside the test bay).

In an embodiment, therefore, the reader contains a protrusion in the cavity, which mates with a recess in the assay device and/or carriage, if present, when the assay device is located at the predetermined reading position. The test kit is designed such that the assay device and/or carriage can be held at a predetermined pre-reading and/or post-reading position away from the reading position and the protrusion.

In this embodiment, the assay device is movable in the direction of insertion into the cavity and perpendicular to the latter direction. In an embodiment the pre-/post-reading position and the reading position are arranged such that the assay device and, if present, the carriage, are conveyed in two dimensions between the pre-/post-reading position and the reading position, upon application of a linear force. The assay device and/or carriage are, in this embodiment, conveyed towards the protrusion at an appropriate angle, e.g. following the angle of any chamfering of the edges of the protrusion, to facilitate a smooth insertion process in a generally linear direction. This provides a further advantage over the insertion process of EP-A-833145, which is not intuitive and is difficult, or at least inconvenient, for the user, because it demands that the user be able to alter accurately the orientation of the test stick with respect to the reader. Such manipulation of the test stick will be especially problematic for users with limited manual dexterity.

In an embodiment the assay device is an elongate test stick.

In an embodiment, the reader and/or assay device and/or carriage comprises means to prevent insertion of the assay device and/or carriage into the cavity in an incorrect orientation, and/or to prevent insertion of the assay device into the carriage in an incorrect orientation. For instance, the cavity may be of a limited width and the carriage, when present, may have an external recess and corresponding protrusion that allows it to slide over the projection housing the reading elements in the cavity in one orientation but not in another orientation. The carriage, when present, may have an internal protrusion which fits into a notch on the assay device only when the assay device is inserted in a correct orientation; in the incorrect orientation, the assay device cannot be inserted sufficiently far into the carriage to allow a recess in the test zone area to line up with the projection housing the reading elements, and so the carriage cannot be fully inserted. Other possibilities will be evident to the skilled person.

In addition to the reading elements for determining the presence and/or absence of analyte in the sample, the reader may also comprise reading means to verify the accurate positioning of the assay device and/or carriage, and optionally display an error message when this positioning is incorrect. These reading means may be optical reading means of the same type discussed above, but located away from the test zone of the assay device.

Referring to FIG. 1, a test apparatus or reader 100 has a housing 101 including an access cover 104 and containing a connection assembly 200 adjacent an inside face of the access cover 104, a reading system 500 and a display system 600.

Figure 2A:
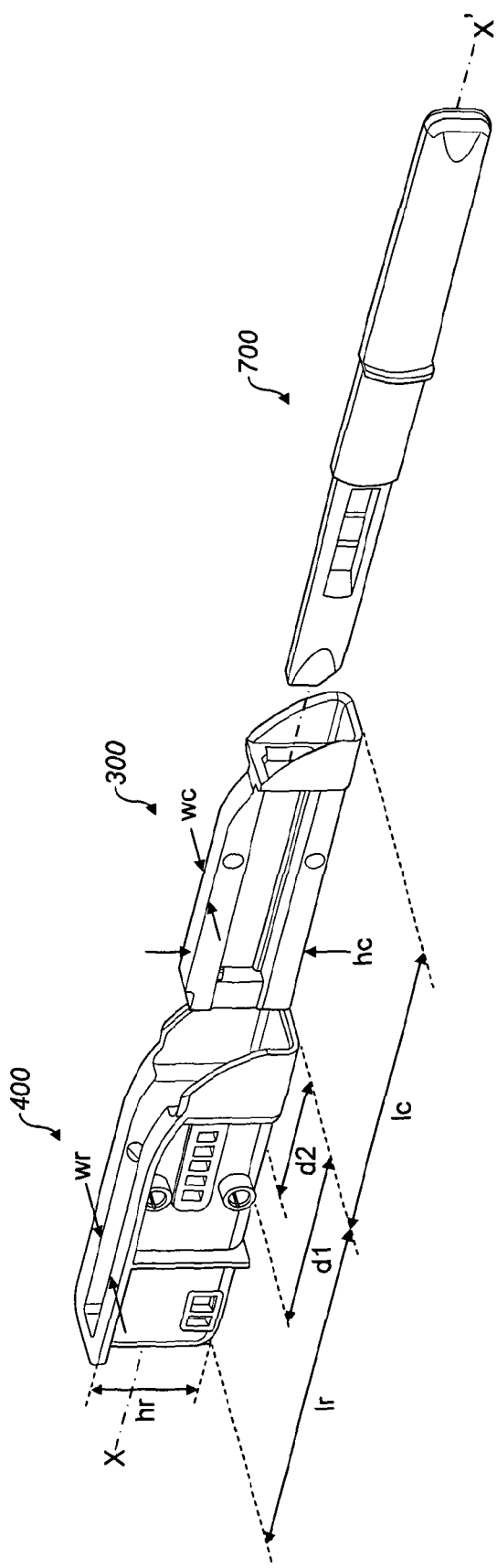
FIGS. 2A and 2B show an exploded view of the connection assembly of FIG. 1 including a carriage and a receptacle, and also an assay device for use with the test apparatus.
Figure 2B:
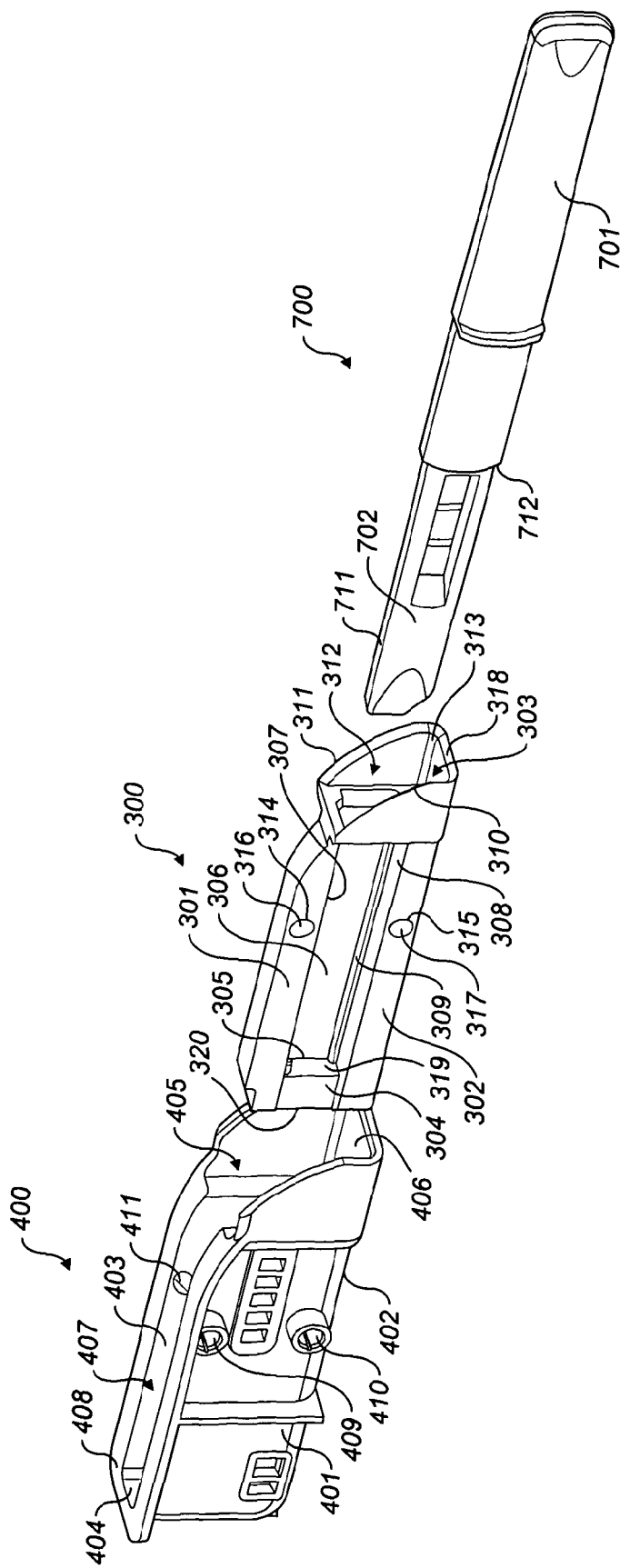

Referring to FIGS. 2A and 2B, the connection assembly 200 of FIG. 1 is co-operable with a test device, which in this embodiment is an assay device 700 provided as a test stick. In this embodiment, the connection assembly 200 consists of first and second separate components 300, 400, having in use a common longitudinal axis X-X'.

Referring to FIGS. 2A, 2B and 3, the first component 300 of the connection assembly 200, referred to hereinafter as a carriage 300, is of unitary construction. The carriage 300 consists of two substantially identical elongate members 301, 302 disposed spaced apart, substantially parallel to axis X-X' and extending from a proximal insertion portion 303 to a distal spacer portion 304, referred to hereinafter as an end stop 304. The end stop 304, which has a proximal face 319 and a distal face 320, links the two elongate members 301, 302 together and maintains them spaced apart. A generally rectangular protrusion 305, referred to hereinafter as a first interference formation 305, has chamfered edges and extends outwardly from and generally perpendicular to the end stop 304.

The elongate members 301, 302 each have upstanding sidewalls to form a channel 306, with the open parts 307, 308 of the channel 306 facing one another and forming a guide 309 having chamfered edges for engagingly receiving the assay device 700.

The insertion portion 303 has two laterally spaced-apart members 310, 311 extending from and between the proximal ends of the elongate members 301, 302 and maintaining them in their parallel disposition. The laterally spaced-apart members 310, 311 define therebetween an opening 312 sized for axial insertion of a distal end portion 702 of the assay device 700. At the opening 312 the chamfered edges of the guide 309 form a step portion 313, referred to hereinafter as a second interference formation 313, adjacent the laterally spaced-apart members 310, 311.

The elongate members 301, 302 have transverse holes 314, 315 disposed at corresponding positions just under halfway from the insertion portion 303 to the end stop 304. A pair of carriage bar magnets 316, 317 are provided. These are secured in respective holes 314, 315. The carriage magnets 316, 317 have an outer configuration matching to the shape of the respective hole 314, 315. In the present embodiment the carriage magnets 316, 317 are right circular cylinders.

In some embodiments, not illustrated, one or more further magnets may be provided on the carriage. For example a further magnet may be provided close to the distal end of the carriage.

The carriage 300 has a height hc defined by the distance between the lower (as illustrated) face of the lower longitudinal member 302 and the upper (as illustrated) face of the upper longitudinal member 301. The carriage 300 has a width we defined by the transverse width of the elongate members 301, 302. The carriage 300 has a length lc defined by the distance from the proximal end to the distal end.

Referring to FIGS. 2A and 2B, the second component 400 of the connection assembly 200, referred to hereinafter as a receptacle 400, is of unitary construction and is configured to receive the carriage 300. The receptacle 400 is generally U-shaped in lateral cross-section and is made up of four wall portions 401-404. The first to third wall portions 401-403 extend axially from a proximal end where they define a proximal opening 405, while the fourth wall portion 404 extends laterally. The first and third wall portions 401, 403 extend mutually parallel to one another from and perpendicular to the second wall portion 402 which defines a generally flat floor portion 406. The fourth wall portion 404 extends perpendicular to the floor portion 406 and also to the first and third wall portions 401, 403 to form a distal end wall 404. Thus the receptacle 400 defines an open channel or cavity 407 having a closed end 404.

In this embodiment the cavity 407 is adjacent the inside face of the access cover 104 of the housing 101.

In this embodiment, the carriage 300 is of opaque moulded plastics. The receptacle 400 is formed of molded plastics and is opaque in this embodiment.

In other embodiments the receptacle may be generally transparent or translucent, or have transparent or translucent portions. The carriage 300 and the receptacle 400 each have additional, laterally-extending flanges 318 (at the insertion portion 303 of the carriage 300) and 408 (around the top (as illustrated) of the first, third and fourth walls, 401, 403, 404 of the receptacle 400) to provide stiffness.

In this embodiment, the cavity 407 has a lateral width wr greater than the lateral width wc of the carriage 300. Also in this embodiment, the length lr of the cavity 407 is greater than the length lc of the carriage 300. The height hc of the carriage 300 and the depth hr of the cavity 407 are such that when the carriage 300 is disposed in the cavity 407 it does not protrude above the flange 408.

In other embodiments, the length of the cavity can be equal to or less than the length of the carriage. Where the cavity is shorter than the carriage, the carriage may protrude from the receptacle.

The first wall 401 carries two anterior bar magnets 409, 410 that are spaced apart in the height direction (as illustrated). It will be seen that the two anterior magnets 409, 410 are a first distance d1 along the cavity 407 from the proximal opening 405. Two posterior bar magnets 411, 412 (412 not shown) are carried by the third wall 403 and similarly spaced apart in the height direction but at a lesser distance d2 along the cavity 407 from the proximal opening 405. The posterior magnets 411, 412, and the anterior magnets 409, 410, coact with the carriage magnets 316, 317.

Where the carriage has one or more further magnets, as discussed above, close to the carriage distal end, further receptacle magnets may be suitably spaced from the posterior magnets to interact with the further magnets of the carriage to latch its distal end to the receptacle.

The length of the cavity 407 is sufficient to receive the carriage 300 in a position where the anterior magnets 409, 410 closely engage with the carriage magnets 316, 317 respectively when the carriage 300 is at least substantially fully longitudinally inserted into the receptacle 400.

Figure 4A:
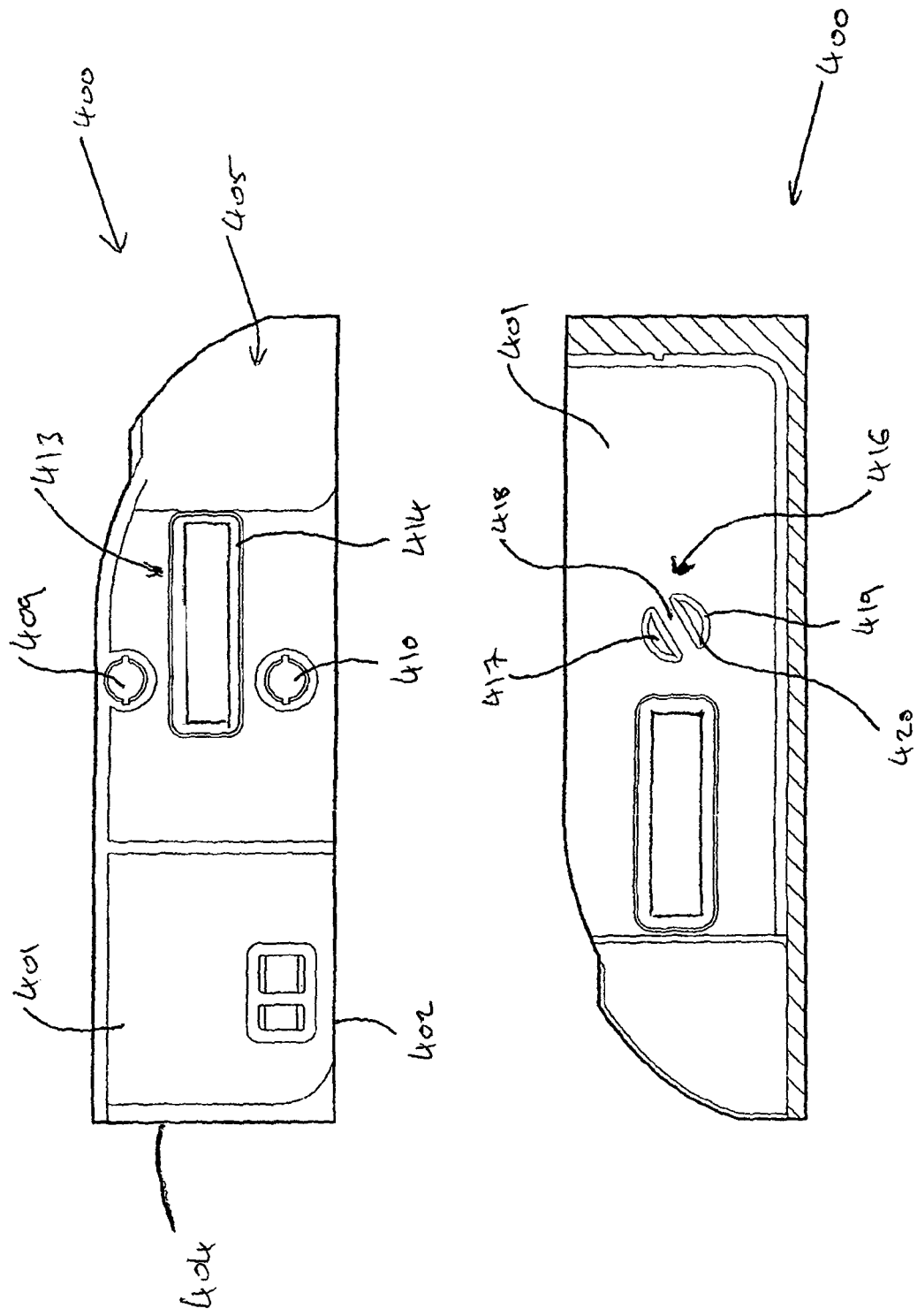
FIG. 4A shows external and internal side elevations of the receptacle of FIGS. 2A and 2B.
Figure 4B:
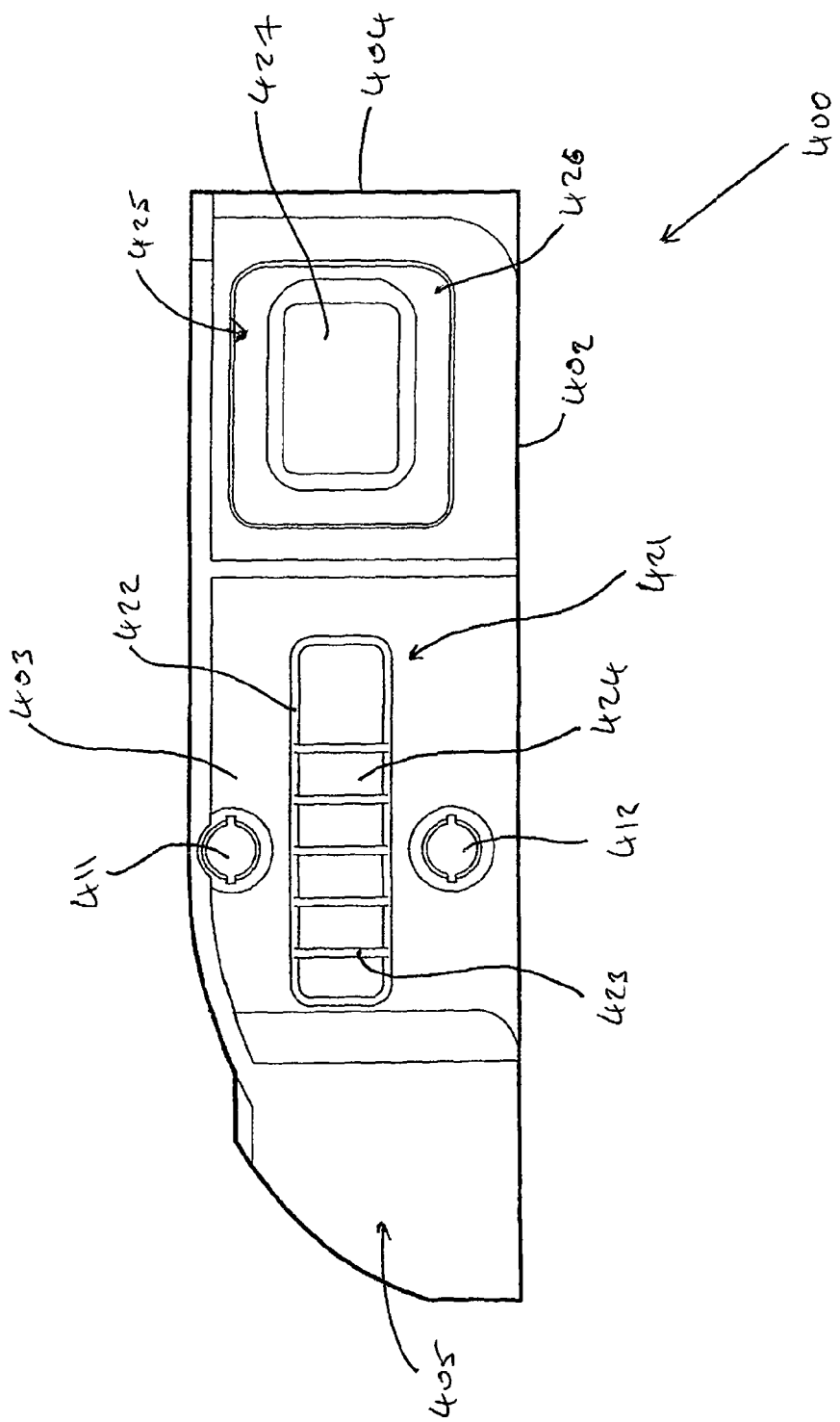
FIG. 4B shows an external side elevation of the receptacle of FIGS. 2A and 2B.
Figure 4C:
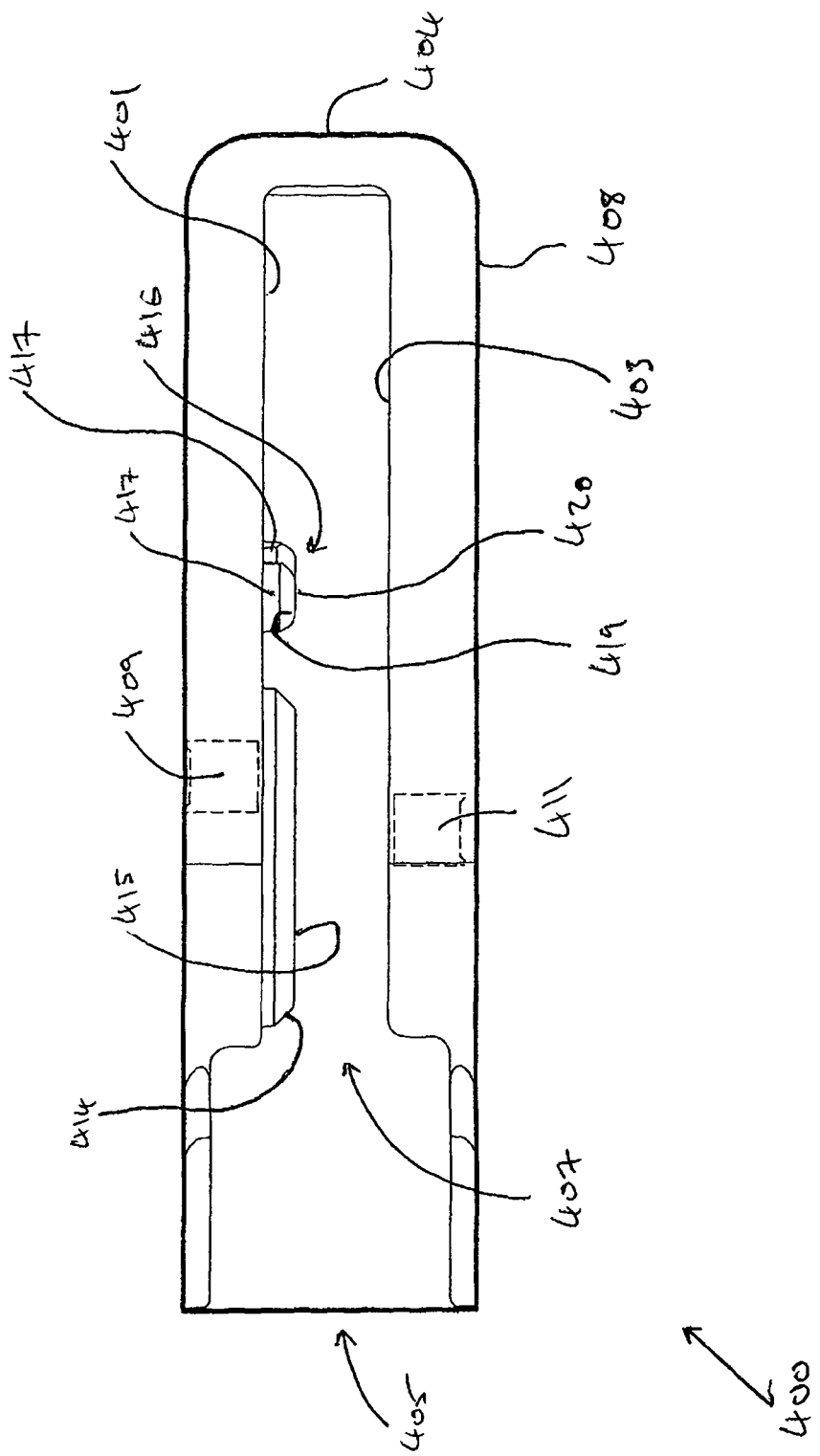
FIG. 4C shows a plan view of the receptacle of FIGS. 2A and 2B.

Referring to FIGS. 4A and 4C, the first wall portion 401 includes an inwardly protruding recessed portion 413, referred to hereinafter as a reading window 413, wherein the thickness of the first wall portion 401 is reduced. The reading window 413 is arranged for co-operation with the reading system 500 and the assay device 700. The reading window 413 is generally rectangular and extends longitudinally from the region of the proximal end of the first wall portion 401 to just under halfway along the first wall portion 401. The reading window 413 has converging chamfered edges 414 which project into the cavity 407 of the receptacle 400. The chamfered edges 414 terminate at, and are joined by, a face 415 of the reading window 413, the face 415 being in a plane parallel to the first wall portion 401 and situated approximately one quarter across the lateral width wr of the cavity 407.

The first wall portion 401 further includes on its inner (as illustrated) surface an inward protrusion 416, referred to hereinafter as a location protrusion 416, situated just over halfway from the proximal end of the first wall portion 401.

The location protrusion 416 has a pair of opposing arcuate lugs 417, the straight sides of which project into the cavity 407 toward the third wall portion 403 of the receptacle 400 and are separated by a gap 418. The curved sides of the arcuate lugs 417 have chamfered edges 419 which also project into the cavity 407. The straight sides and chamfered edges 419 converge together and terminate at tapered ends 420 of the arcuate lugs 417. The tapered ends 420 are situated approximately one quarter across the lateral width wr of the cavity 407.

Referring to FIGS. 4B and 4C, the third wall portion 403 includes an inwardly recessed portion 421, referred to hereinafter as an illumination window 421, wherein the thickness of the third wall portion 403 is reduced. The illumination window 421 is arranged for co-operation with the reading system 500 and the assay device 700. The illumination window 421 is generally rectangular and extends longitudinally from the region of the proximal end of the third wall portion 403 to approximately halfway along the third wall portion 403. The illumination window 421 has converging chamfered edges 422 which project into the third wall portion 403. The illumination window 421 includes a plurality of strengthening ridges 423 extending between the upper and lower (as illustrated) chamfered edges 422 such as to form a series of recessed segments 424 along the illumination window 421.

The third wall portion 403 further includes an outwardly protruding recessed portion 425, referred to hereinafter as an accommodation formation 425, wherein the thickness of the third wall portion 403 is reduced. The accommodation formation 425 is generally rectangular and extends longitudinally from the distal end of the third wall portion 403 to approximately one third of the way along the third wall portion 403. The accommodation formation 425 has converging chamfered edges 426 which project outwardly from the third wall portion 403. The chamfered edges 426 terminate at, and are joined by, a face 427 of the accommodation formation 425, the face 427 being in a plane parallel to the third wall portion 403 and situated approximately halfway between the third wall portion 403 and the outer lateral extremity of the flange 408. The accommodation formation 425 is of sufficient width and depth to accommodate the laterally extending first interference formation 305 of the carriage 300 when the carriage 300 is adjacent to the third wall portion 403.

Figure 9:
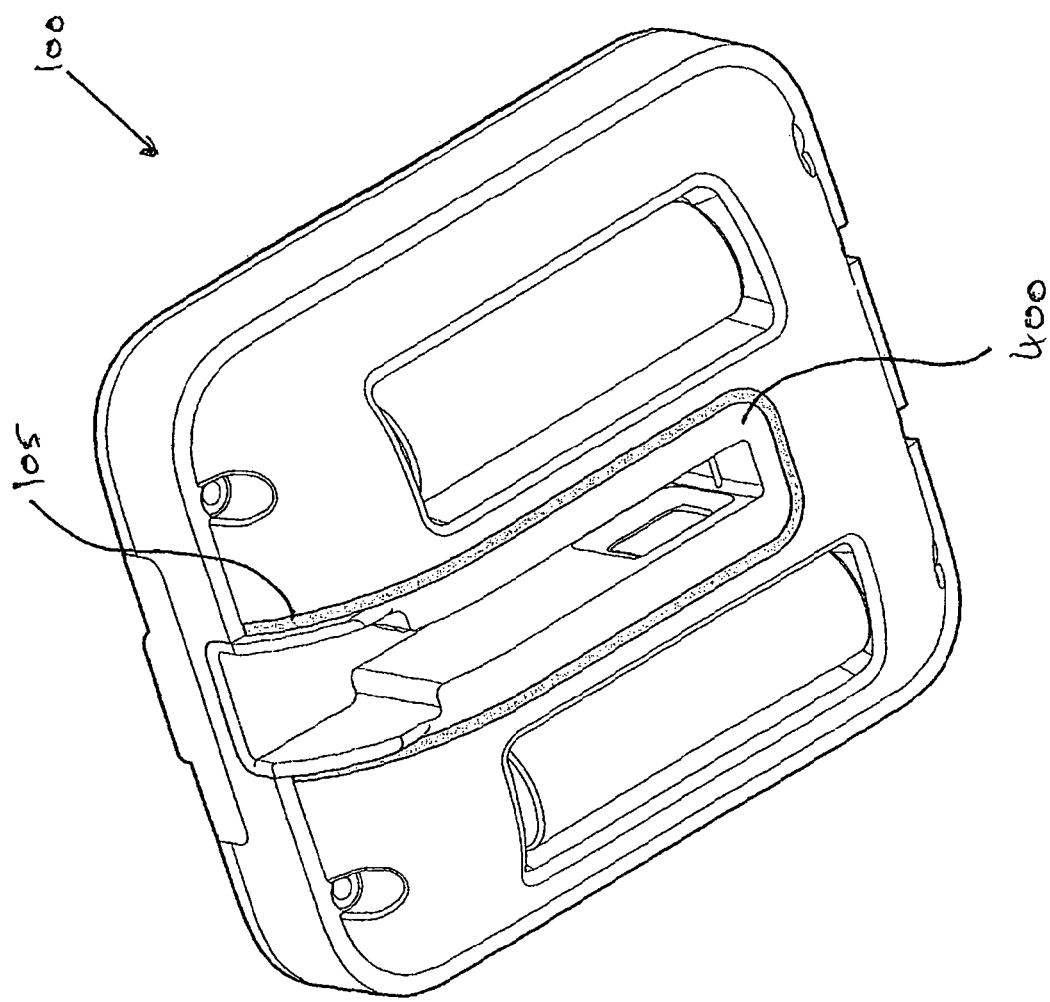
FIG. 9 shows a perspective view of the underside of the test apparatus of FIG. 1.

Referring to FIG. 9, there is in this embodiment an overmoulded seal 105 on the housing 101 which is abutted by the receptacle 400.

Referring to FIG. 5A, an assay device 700 hereinafter referred to as a test stick is a generally flat and elongate body formed of plastics and includes a proximal end 701 suitable for handling by a user and a distal end 702 for co-operation with the carriage 300 and receptacle 400.

The test stick 700 includes a first recessed portion 703, hereinafter referred to as a reading zone or detection portion 703, for a sample to be tested. The detection portion 703 extends longitudinally from a position approximately 18 percent of the way from the distal end 702 to a position approximately 34 percent of the way from the distal end 702. The detection portion 703 has chamfered edges 704 which extend into the body of the test stick 700 and are co-operable with the chamfered edges 414 of the reading window 413.

The test stick 700 further includes a second recessed portion 705, hereinafter referred to as a location seat (or recess) 705, situated between the distal end 702 and the detection portion 703. The location seat 705 has a pair of opposing, arcuate recessed portions 706 separated by a bridge 707. The arcuate recessed portions 706 and the bridge 707 have chamfered edges 708 which extend into the body of the test stick 700 and are co-operable with the location protrusion 416 of the first wall portion 401 of the receptacle 400.

Referring to FIG. 5B, the test stick 700 includes a third recessed portion 709, hereinafter referred to as an illumination recess 709, for co-operation with the illumination window 421 of the third wall portion 403 of the receptacle 400 and with the reading system 500. The illumination recess 709 extends longitudinally from a position approximately 17 percent of the way from the distal end 702 to a position approximately 37 percent of the way from the distal end 702. The illumination recess 709 has chamfered edges 710 which extend into the body of the test stick 700. The depth of the illumination recess 709 in the body of the test stick 700 is greater than the depth of the detection portion 703.

The test stick 700 further includes angled upper and lower (as illustrated) edges 711 for engagement with the chamfered edges of the guide 309 of the carriage 300.

Figure 6:
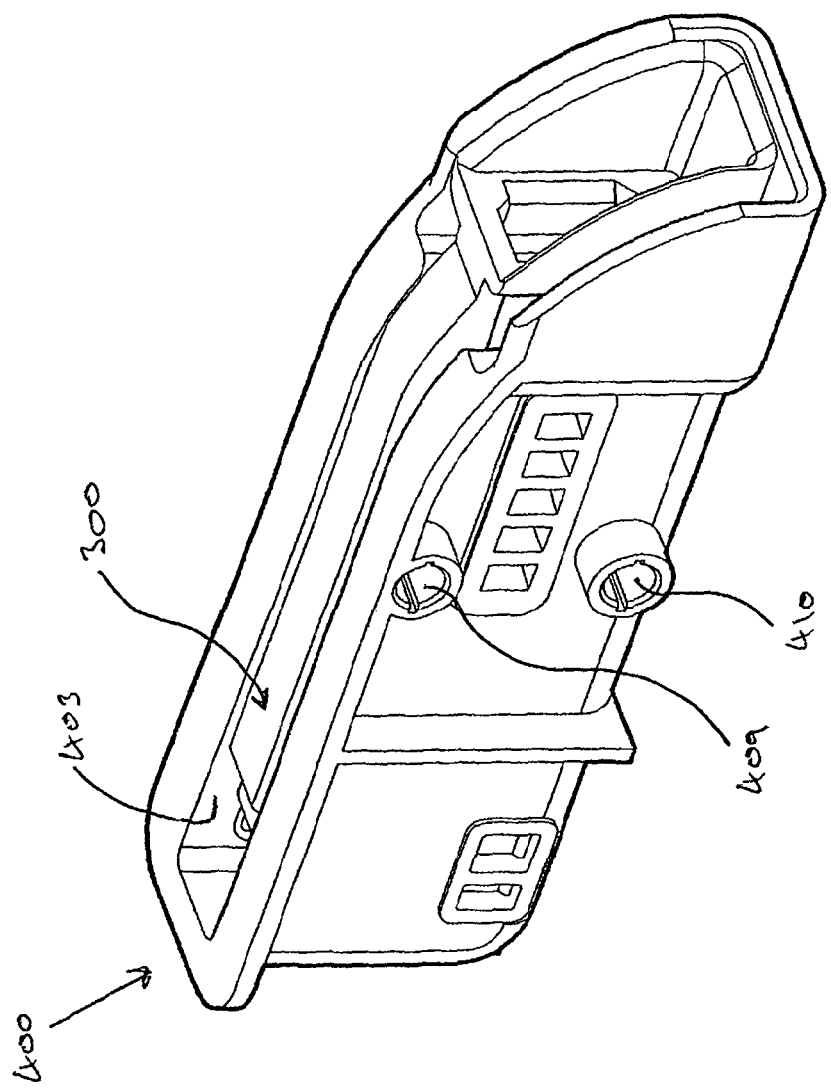
FIG. 6 shows a perspective view of the carriage in a first position with respect to the receptacle.

Referring to FIG. 6, the carriage 300 is in a first position in the cavity 407, referred to hereinafter as a pre-reading or storage position, wherein the carriage 300 abuts the third wall portion 403 of the receptacle 400. In the pre-reading position, which is the normal condition prior to (and after) use of the test apparatus 100, the magnetic means formed by the carriage magnets 316, 317 and the anterior magnets 409, 410 causes the carriage to be latched in the pre-reading position at the third wall portion 403. Also, in the pre-reading position, the first interference formation 305 of the carriage 300 is situated within the accommodation formation 425 of the third wall portion 403 of the receptacle 400.

In use, a user applies the sample to be tested to the test stick 700 as appropriate such that sample material becomes situated on the detection portion 703 of the test stick 700. In this embodiment, the sample material is urine and the analytes are hormones.

Figure 7:
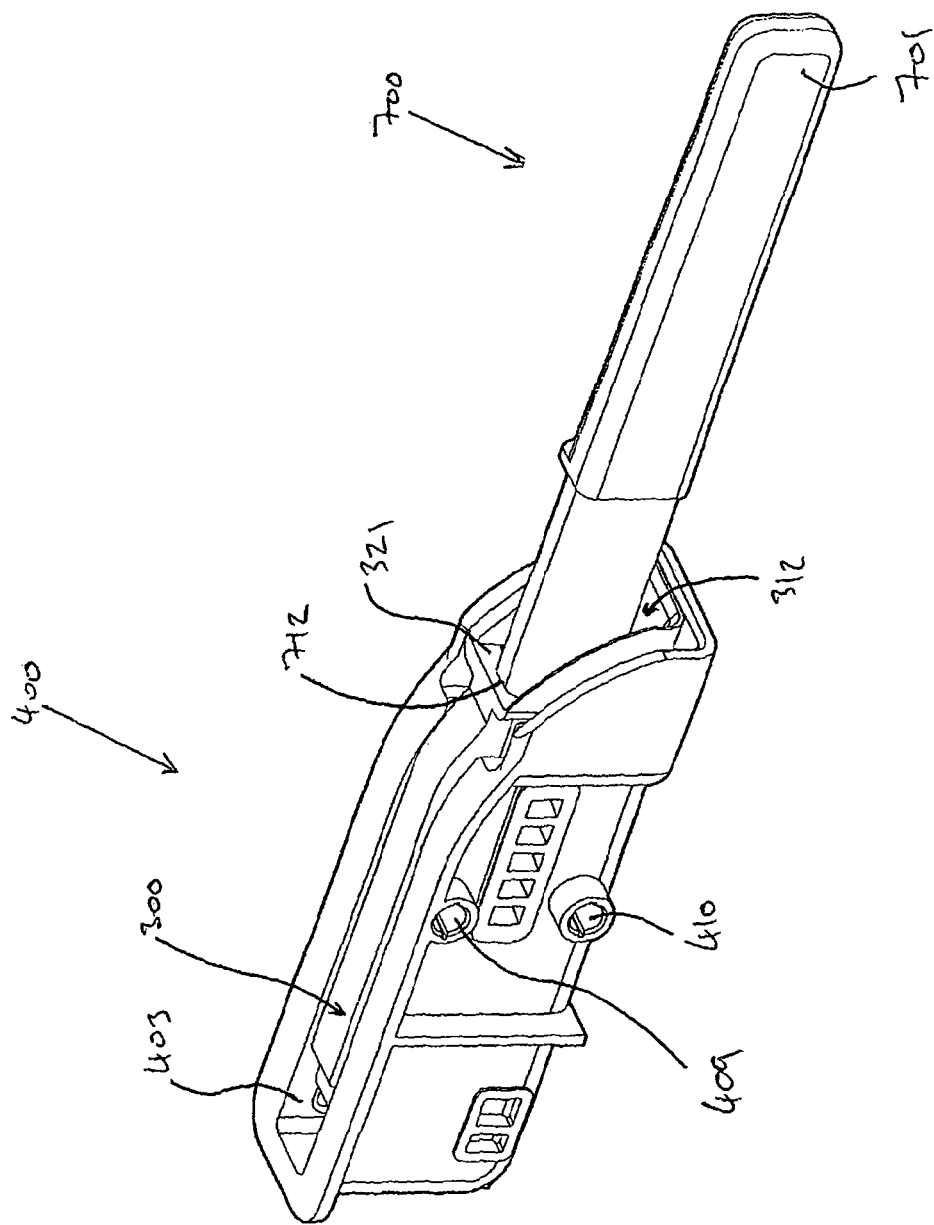
FIG. 7 shows a perspective view of the carriage in the first position with respect to the receptacle, and a portion of the assay device in the carriage.

Referring to FIG. 7, the user then inserts the distal end portion 702 of the test stick 700 into the opening 312 of the carriage 300 such that the guide 309 is engaged by the angled upper and lower edges 711 of the test stick 700. The second interference formation 313 prevents the user from inserting the test stick 700 in an incorrect orientation. The user pushes the proximal end 701 of the test stick 700 so as to urge the test stick 700 through the channel 306, the test stick 700 being free to slide along the guide 309 until a shoulder 712 of the test stick 700 comes into abutment with a shoulder abutment face 321 of the opening 312 of the carriage 300. Simultaneously, a distal end face 713 of the test stick 700 comes into close proximity with the proximal face 319 of the end stop 304 (see also FIGS. 2A, 2B and 5A). The force so imparted to the carriage 300 by the test stick 700 overcomes the attraction force between the carriage magnets 316, 317 and the posterior magnets 411, 412, causing the carriage 300 to become unlatched from the third wall portion 403 and to move longitudinally with respect to the receptacle 400 toward the anterior magnets 409, 410.

Figure 8:
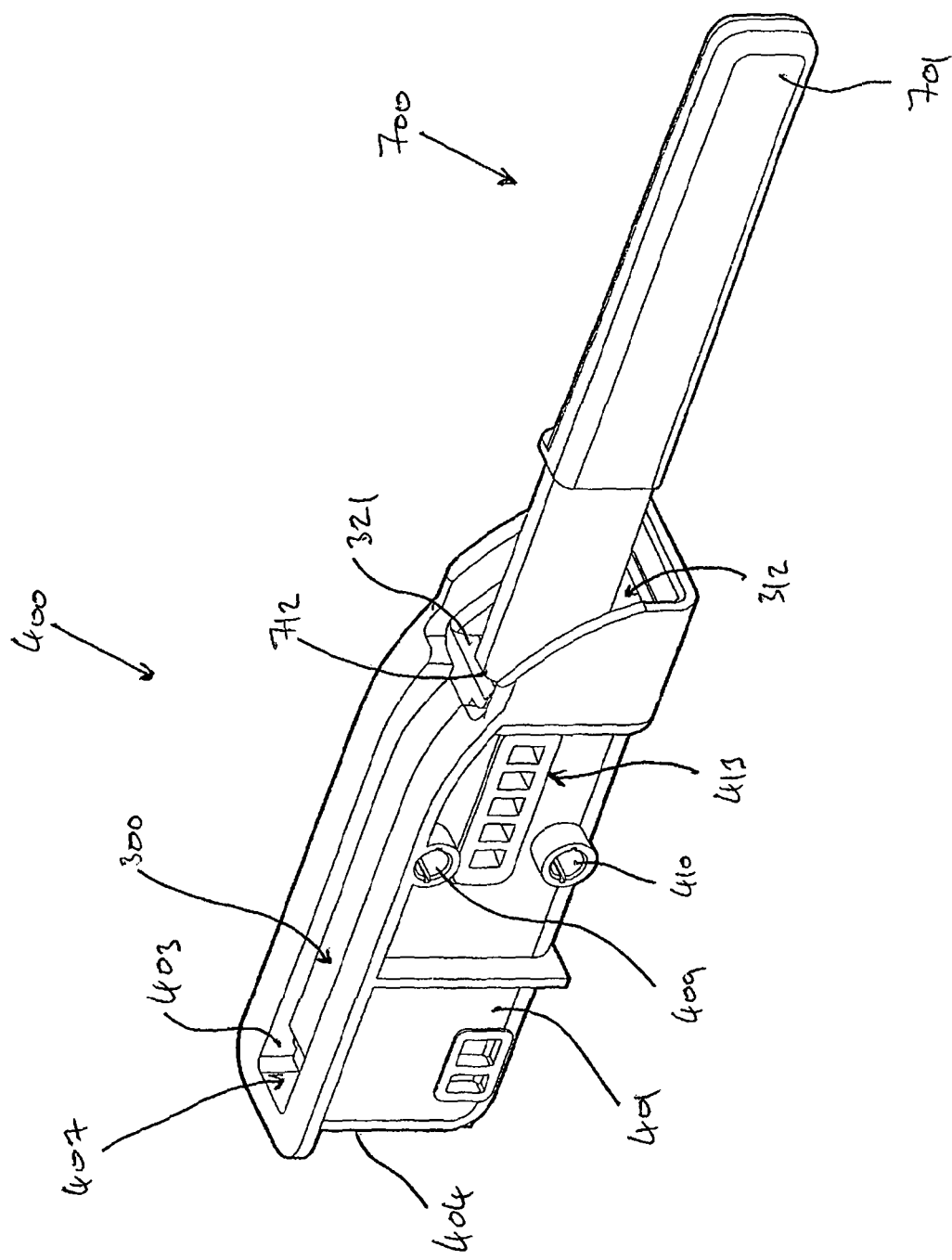
FIG. 8 shows a perspective view of the carriage in a second position with respect to the receptacle, and a portion of the assay device in the carriage.

Referring to FIG. 8, attraction between the carriage magnets 316, 317 and the anterior magnets 409, 410, causes the carriage 300 to separate from the third wall portion 403 and to move laterally across the cavity 407 to abut the first wall portion 401. The magnetic means formed by the carriage magnets 316, 317 and anterior magnets 409, 410 thus cause the carriage 300 to latch to the first wall portion 401. In so doing, the chamfered edges 704 of the detection portion 703 of the test stick 700 engage the chamfered edges 414 of the reading window 413, thereby aligning the detection portion 703 with the face 415 of the reading window 413. Similarly, the illumination recess 709 of the test stick 700 is aligned with the illumination window 421. Simultaneously, the chamfered edges 708 of the arcuate recessed portions 706 and the bridge 707 (of the location seat 705 of the test stick 700) engage the chamfered edges 419 of the arcuate lugs 417 of the first wall portion 401 of the receptacle 400, and the bridge 707 is received by the gap 418. Also, the first interference formation 305 of the carriage 300 is simultaneously withdrawn from the accommodation formation 425 of the third wall portion 403 of the receptacle 400. In addition, in this embodiment, there is a clearance of approximately 0.5 mm between the distal face 320 of the end stop 304 and the inner (as illustrated) surface of the fourth wall portion 404 of the receptacle 400.

Thus, the carriage 300 comes to rest in a predetermined position in the cavity 407, referred to hereinafter as a reading position, wherein the carriage 300 abuts the first wall portion 401 of the receptacle 400. In this reading position the illumination recess 709 and the detection portion 703 of the test stick 700, and thereby the sample material to be tested, are correctly aligned for use with the reading system 500. An audible "click" is produced as the carriage magnets 316, 317 latch to the anterior magnets 409, 410, and the chamfered edges 704, 414, 708, 418 are engaged, confirming to the user that the detection portion 703 of the test stick 700 is correctly situated in the reading position.

As noted above, embodiments having further magnets on both carriage and receptacle may be provided to reduce any lateral movement of the distal part of the carriage.

The reading system 500 includes a light source system such as one or more LEDs and a sensor system such as one or more photodiodes to detect whether the carriage 300 is correctly seated against the receptacle 400 when in the reading position. The LED shines a beam of light onto the carriage 300 and any reflected light is measured by the photodiode. If the carriage 300 is not in the correct position (for example, because there is debris in the receptacle cavity 407) then the angle of the reflected light will cause the photodiode to detect a different quantity of light than expected. Thus there is a relationship between the width of the light beam, the relative positioning of the photodiode and LED, and the angle of the reflected light.

The display system 600 includes an LCD screen for displaying information relating to the data obtained by the reading system 500.

Once the reading system 500 has taken the desired readings suitable for use by the display system 600, the user pulls the proximal end 701 of the test stick 700 away from the receptacle 400, causing the chamfered edges 704, 414, 708, 418 to ride over and release from each other. The force so imparted on the test stick 700 overcomes the attraction force between the carriage magnets 316, 317 and the anterior magnets 409, 410 allowing the carriage 300 to unlatch and separate from the first wall portion 401 and to move laterally and longitudinally with respect to the receptacle 400. In so doing, the first interference formation 305 of the carriage 300 is drawn into the accommodation formation 425 of the third wall portion 403 of the receptacle 400. Also, the distal face 320 of the end stop 304 moves away from the inner (as illustrated) surface of the fourth wall portion 404. Attraction between the carriage magnets 316, 317 and the posterior magnets 411, 412 draws the carriage 300 to further move longitudinally with respect to the receptacle 400. Consequently, the magnetic means formed by carriage magnets 316, 317 and posterior magnets 411, 412 latch the carriage at the third wall portion 403 in the pre-reading or storage position defined above. An audible "click" is produced, confirming to the user that the carriage 300 is in the correct storage position. As previously stated, in this storage position the test stick 700 is free to slide longitudinally along the guide 309 through the channel 306 of the carriage 300, hence the test stick 700 can be withdrawn fully from the opening 312 of the carriage 300 upon continued application by the user of the pulling force. The test stick 700 can subsequently be discarded by the user.

Thus, the embodiment described provides a means for accurate and repeatable positioning of a test stick (or a series of individual, disposable test devices each including the features of the test stick 700 described) relative to a reading system. Advantageously, the features of the embodiment described enable a user to insert the test stick 700 into the carriage 300, and to move the carriage 300 from the pre-reading or storage position to the reading position, in one continuous, generally linear movement. Similarly, the features of the embodiment enable the user to move the carriage 300 from the reading position to the storage position, and to withdraw the test stick 700 from the carriage 300, in one continuous, generally linear movement. Furthermore, the magnetic means provide for latching of the carriage 300 to the receptacle 400 with minimal friction. Thus, the type of wear experienced in the device of the prior art is avoided, thereby offering increased accuracy and longevity of the test apparatus 100. A further advantage is that the continuous movement described is more simple and convenient for the user than the multistage insertion process of the prior art.

As described above, in this embodiment the cavity 407 is adjacent the inside face of the access cover 104. This allows any sample material which leaks from the receptacle 400 to drain away from the test apparatus 100, thereby avoiding contamination of the test apparatus 100. In addition, the overmoulded seal 105 between the housing 101 and the receptacle 400 prevents the ingress of sample material to the housing 101 and the components therein.

Repeated use of the test apparatus 100 tends to cause sample material to accumulate on the carriage 300 which interferes with the movement and/or magnetic latching of the carriage 300 in the receptacle 400, and/or the movement of the test stick 700 in the carriage 300. Therefore, in one embodiment, the carriage 300 is releasably secured in the receptacle 400 so that it can be removed and cleaned by a user and subsequently reinstalled in the receptacle 400. The user gains access to the carriage 300 by removing the access cover 104 and sliding the carriage 300 out of the receptacle 400. The first interference formation 305 of the carriage 300 interacts with the reading window 413 to prevent the user from reinserting the carriage 300 into the receptacle 400 in an incorrect orientation. In another embodiment, the test apparatus 100 includes detection and indication means to determine that the reading window 413 and/or illumination window 421 needs to be cleaned and to alert the user to that need.

In some embodiments the carriage is secured non-releasably in the cavity, or is secured in a way that requires tools to release it.

In an embodiment, the carriage 300 and the receptacle 400 are each formed of one or more of the following plastics: Acrylonitrile Butadiene Styrene (ABS), Polycarbonate Alloy (PC), Polycarbonate Alloy/Acrylonitrile Butadiene Styrene (PC/ABS), acetal, Polybutylene Terephtalate (PBT).

In an embodiment, the carriage 300 and/or receptacle 400 is not of unitary construction but rather consists of at least two component pieces joined together, e.g. by welding, fusion bonding, adhesive bonding, mechanical fastening, or other suitable means which will be apparent to a person skilled in the art.

In an embodiment, the strengthening ridges 423 are excluded from the illumination window 421.

In an embodiment, the carriage 300 and/or receptacle 400 is not moulded but rather is formed by casting, machining, or other suitable means which will be apparent to a person skilled in the art.

In an embodiment, at least one of the magnets 316, 317, 409, 410, 411, 412 is an electromagnet. In another embodiment, at least one of the magnets 316, 317, 409, 410, 411, 412 is replaced by a magnetic member constructed from a suitable magnetic material (e.g. iron, nickel or cobalt, or an alloy thereof). In another embodiment, at least one pair of the magnets 316, 317, 409, 410, 411, 412 and/or members are separated (e.g. by the first or third wall portions 401, 403 or the elongate members 301, 302 of the carriage 300) so as not to come into direct contact with each other. In another embodiment, at least one of the magnets 316, 317, 409, 410, 411, 412 and/or magnetic members is elongate and extends along the longitudinal axis X-X' of the carriage 300 and the receptacle 400. In another embodiment, at least one of the magnets 316, 317, 409, 410, 411, 412 is replaced by alternative latching means, for example a sprung pin or other suitable means which will be apparent to a person skilled in the art.

In an embodiment, the reading system 500 is one of: a fluorescent system, a camera system (visual), and a reflective system.

In an embodiment, there is provided a plurality of reading positions and/or storage positions.

A specific and non-limiting example of some physical properties of an embodiment is given below.

EXAMPLE

The dimensions of the cavity 407 of the receptacle 400 are: length 62 mm, width 7 mm, depth 18 mm. The dimensions of the carriage 300 are: length 58.5 mm, width 5.2 mm, depth 17 mm.

Each of the anterior and posterior magnets 409, 410, 411, 412 is constructed from neodymium iron boron with NiCuNi plating grade N42, and has a length of 4 mm and a diameter of 3 mm. Each of the carriage magnets 316, 317 is constructed from corrosion-resistant samarium grade SmCo26, and has a length of 5 mm and a diameter of 3 mm.

The anterior magnets 409, 410 and the posterior magnets 411, 412 are at respective distances of 29.5 mm and 26.5 mm from the proximal opening 405 of the receptacle 400, i.e. they are longitudinally offset by 3 mm. The anterior magnets 409, 410 and the posterior magnets 411, 412 are respectively spaced 13 mm apart in the height direction. Each of the carriage magnets 316, 317 is spaced 6.5 mm from a central, longitudinal axis of the channel 306 such that they are spaced apart in the height direction by 13 mm. Thus the carriage magnets 316, 317 have between them the same height spacing as the anterior magnets 409, 410 and the posterior magnets 411, 412.

In other embodiments there is no magnetic latching in the pre-reading position. Other securing means may retain it in the pre-reading position if required.

Another set of embodiments does not use a carriage but includes magnets on the assay device itself that cause the assay device—for example a test device somewhat similar in shape to a credit card- to become latched in the reading position by interaction with magnets in the walls defining the cavity. In one example of this set, a card-like test device, incorporating one or more magnets is inserted into a slot in a reader. It is pulled into the correct latched reading position by the magnets on the walls of the slot interacting with the or each magnet on or in the card. Of course, the invention is not limited to any particular configuration of assay device.

The invention is not restricted to the features of the embodiments shown or described.

The invention claimed is:
1. A reader comprising
a housing having a cavity, the cavity extending longitudinally from a proximal opening of the housing;
a carriage movably coupled to the housing; said carriage adapted for receiving at least a portion of a test stick;
a reading element, located within the housing, for reading a test zone of the test stick when the reading element and the test zone are aligned; and
first carriage magnetic means on the carriage, first housing magnetic means on the housing, which first housing magnetic means co-operate with the first carriage magnetic means on the carriage, for latching the carriage onto the housing within said cavity at a predetermined reading position and
second housing magnetic means on the housing and longitudinally spaced from the first housing magnetic means, which second housing magnetic means co-operate with the first carriage magnetic means on the carriage, for latching the carriage onto the housing at a predetermined pre-reading and/or post-reading position,
wherein the predetermined reading position is a position where the test zone is aligned with the reading element and the predetermined pre-reading and/or post-reading position is a position where the test zone is not aligned with the reading element, and wherein the predetermined pre-reading and/or post-reading position is longitudinally spaced apart from the predetermined reading position.

2. The reader according to claim 1, wherein the reading element comprises optical reading means.

3. The reader according to claim 1 or 2, wherein the first housing magnetic means and/or, the second housing magnetic means are provided in or adjacent to the cavity.

4. The reader according to claim 1, wherein the carriage is adapted to be received in the cavity of the reader.

5. The reader according to claim 4, wherein the carriage is removable from the cavity of the reader.

6. The reader according to claim 1, wherein the carriage forms at least one wall of the cavity.

7. The reader according to claim 1, wherein the housing of the reader has a protrusion in the cavity which mates with a recess in the test stick and/or the carriage when the test stick is located at the predetermined reading position.

8. The reader according to claim 1, wherein the pre-/post-reading position and the predetermined reading position are arranged such that a test stick and the carriage are conveyed in two dimensions between the pre-/post-reading position and the predetermined reading position.

9. A test kit comprising a test stick having a test zone and a reader, the reader comprising
a housing having a cavity, the cavity extending longitudinally from a proximal opening of the housing;
a carriage movably coupled to the housing; said carriage adapted for receiving at least a portion of the test stick;
a reading element, located within the housing, for reading the test zone of the test stick when the reading element and the test zone are aligned; and
first carriage magnetic means on the carriage, first housing magnetic means on the housing, which first housing magnetic means co-operate with the first carriage magnetic means on the carriage, for latching the carriage onto the housing within said cavity at a predetermined reading position and
second housing magnetic means on the housing and longitudinally spaced from the first housing magnetic means, which second housing magnetic means co-operate with the first carriage magnetic means on the carriage, for latching the carriage onto the housing at a predetermined pre-reading and/or post-reading position,
wherein the predetermined reading position is a position where the test zone is aligned with the reading element and the predetermined pre-reading and/or post-reading position is a position where the test zone is not aligned with the reading element, and wherein the predetermined pre-reading and/or post-reading position is longitudinally spaced apart from the predetermined reading position.

10. The test kit according to claim 9, wherein the reader is configured to detect a change at a test zone of the test stick caused by the one or more analytes during performance of an assay only when the test stick is located at the predetermined reading position.

11. The test kit according to claim 9 or 10, wherein the reading element comprises optical reading means.

12. The test kit according to claim 9, wherein the test stick comprises a porous carrier and/or microfluidic flow path.

13. The test kit according to claim 9, wherein the first housing magnetic means and/or, the second housing magnetic means are provided in or adjacent to the cavity.

14. The test kit according to claim 9, wherein the carriage is adapted to be received in the cavity of the reader.

15. The test kit according to claim 14, wherein the carriage is removable from the cavity of the reader.

16. The test kit according to claim 9, wherein the carriage forms at least one wall of the cavity.

17. The test kit according to claim 9, wherein the housing of the reader contains a protrusion in the cavity which mates with a recess in the test stick and/or carriage when the test stick is located at the predetermined reading position.

18. The test kit according to claim 9, wherein the pre-/post-reading position and the predetermined reading position are arranged such that the test stick and the carriage are conveyed in two dimensions between the pre-/post-reading position and the predetermined reading position.

19. The reader according to claim 1, wherein the housing has a protrusion in the cavity, and the protrusion mates with a recess in a test stick and/or in the carriage when the test stick is located at the predetermined reading position and wherein the predetermined pre-reading and/or post-reading position is spaced apart from the protrusion.

20. The test kit according to claim 9, wherein the housing has a protrusion in the cavity, and the protrusion mates with a recess in the test stick and/or carriage when the test stick is located at the predetermined reading position and wherein the predetermined pre-reading and/or post-reading position is spaced apart from the protrusion.

21. The reader according to claim 1, wherein the first carriage magnetic means and the first housing magnetic means are configured such that an audible signal is generated as the carriage is latched onto the housing at the predetermined reading position to confirm to a user that a test stick is correctly situated in the predetermined reading position.

22. The test kit according to claim 9, wherein the first carriage magnetic means and the first housing magnetic means are configured such that an audible signal is generated as the carriage is latched onto the housing at the predetermined reading position to confirm to a user that the test stick is correctly situated in the predetermined reading position.

23. The reader according to claim 8, wherein the pre-/post-reading position and the predetermined reading position are arranged such that a test stick and the carriage are conveyed in two dimensions between the pre-/post-reading position and the predetermined reading position upon application of a linear force.

24. The test kit according to claim 18, wherein the pre-/post-reading position and the predetermined reading position are arranged such that a test stick and the carriage are conveyed in two dimensions between the pre-/post-reading position and the predetermined reading position upon application of a linear force.

* * * * *